(12) United States Patent
Chiang et al.

(10) Patent No.: US 8,945,638 B2
(45) Date of Patent: Feb. 3, 2015

(54) ALCOHOL EXTRACT OF DEHULLED ADLAY SEEDS FOR TREATING GASTRIC ULCER AND/OR STOMACH CANCER

(75) Inventors: Wenchang Chiang, Kaohsiung (TW); Yueh-Hsiung Kuo, Kaohsiung (TW); Yun-Lian Lin, Kaohsiung (TW); Cheng-Pei Chung, Kaohsiung (TW)

(73) Assignee: Joben Bio-Medical Co., Ltd., Pingtung County (TW)

( * ) Notice: Subject to any disclaimer, the term of this patent is extended or adjusted under 35 U.S.C. 154(b) by 342 days.

(21) Appl. No.: 13/304,566

(22) Filed: Nov. 25, 2011

(65) Prior Publication Data
US 2013/0136812 A1    May 30, 2013

(51) Int. Cl.
*A61K 36/8994* (2006.01)
(52) U.S. Cl.
USPC .......................................... 424/750; 424/776
(58) Field of Classification Search
CPC ................................................. A61K 36/8994
USPC .................................................. 424/750, 776
See application file for complete search history.

(56) References Cited

FOREIGN PATENT DOCUMENTS

WO    WO 00/69452 A1 * 11/2000

OTHER PUBLICATIONS

Sarker, ed. (Natural Product Isolation, 2nd ed. New Jersey: Humana Press. 2006. pp. 323-327).*
Office action and search report issued on Aug. 22, 2013 to the corresponding Taiwan Application No. 100138736.
Ming-Yi Lee, Isolation and identification of antitumor and anti-inflammatory active components from adlay bran, pp. 75-76, Jul. 2008.
English abstract translation of Ming-Yi Lee, Isolation and identification of antitumor and anti-inflammatory active components from adlay bran, 2008.
Handan Bekdemir et al., Cox-2 Expression in Gastric Cancer, International Journal of Hematology and Oncology, vol. 20, No. 1, pp. 34-41, 2010.
Rafael F. Perini et al., Mucosal Repair and COX-2 Inhibition, Current Pharmaceutical Design, vol. 9, pp. 2207-2211, 2003.
Cheng-Pei Chung et al., Gastroprotective Activities of Adlay (*Coix lachryma-jobi* L. var. ma-yuen Stapf) on the Growth of the Stomach Cancer AGS Cell Line and Indomethacin-Induced Gastric Ulcers, Journal of Agricultural and Food Chemistry, 2011, pp. 6025-6033, vol. 59.
R. O. Nneli et al., Diets/Dietary Habits and Certain Gastrointestinal Disorders in the Tropics: A Review, Nigerian Journal of Physiological Sciences, 2007, pp. 1-13, vol. 22.
Muriel Primon De Barros et al., Evaluations of antiulcer activity of the main phenolic acids found in Brazilian Green Propolis, Journal of Ethnopharmacology, 2008, pp. 372-377, vol. 120.
Dipak Das et al., Hydroxyl Radical is the Major Causitive Factor in Stress-Induced Gastric Ulceration, Free Radical Biology & Medicine, 1997, pp. 8-18, vol. 23, No. 1.
M. Halici et al., Effects of water extrct of *Usnea longissima* on antioxidant enzyme activity and mucosal damage caused by indomethacin in rats, Phytomedicine, 2005, pp. 656-662, vol. 12.
Wenchang Chiang et al., Effects of Dehulled Adlay on the Culture Count of Some Microbiota and Their Metabolism in the Gastrointestinal Tract of Rats, J. Agric. Food Chem., 2000, pp. 829-832, vol. 48, No. 3.
Ming-Yi Lee et al., Anti-tumor and Anti-inflammatory Activity of the Methanol Extracts from Adlay Bran, Food Science and Biotechnology, 2008, pp. 1-7, vol. 17, No. 6.
Ching-Chuan Kuo et al., Antagonism of Free-Radical-Induced Damage of Adlay Seed and Its Antiproliferative Effect in Human Histolytic Lymphoma U937 Monocytic Cells, J. Agric. Food Chem., 2001, pp. 1564-1570, vol. 49, No. 3.
Tien-Tso Wu et al., Determination of the contents of the main biochemical compounds of Adlay (*Coxi lachrymal-jobi*), Food Chemistry, 2007, pp. 1509-1515, vol. 104.
Hsin-Yi Hsu et al., Suppression of Allergic Reactions by Dehulled Adlay in Association with the Balance of Th1/Th2 Cell Responses, Journal of Agricultural and Food Chemistry, 2003, pp. 3763-3769, vol. 51, No. 13.
Din-Wen Huang et al., Effect of Adlay (*Coix lachryma-jobi* L. var. ma-yuen Stapf) Testa and Its Phenolic Components on Cu2+-Treated Low-Density Lipoprotein (LDL) Oxidation and Lipopolysaccharide (LPS)-Induced Inflammation in RAW 264.7 Macrophages, Journal of Agricultural and Food Chemistry, 2009, pp. 2259-2266, vol. 57, No. 6.
Din-Wen Huang et al., Identification of Compounds in Adlay (*Coix lachryma-jobi* L. var. ma-yuen Stapf) Seed Hull Extracts That Inhibit Lipopolysaccharide-Induced Inflammation in Raw 264.7 Macrophages, Journal of Agricultural and Food Chemistry, 2009, pp. 10651-10657, vol. 57, No. 22.
Hong-Jhang Chen et al., Anti-inflammatory effects and chemical study of a flavonoid-enriched fraction from adlay bran, Food Chemistry, 2011, pp. 1741-1748, vol. 126.
Hong-Jhang Chen et al., Mast Cell-Dependent Allergic Responses Are Inhibited by Ethanolic Extract of Adlay (*Coix lachryma-jobi* L. var. ma-yuen Stapf) Testa, Journal of Agricultural and Food Chemistry, 2010, pp. 2596-2601, vol. 58, No. 4.
Chun-Kuang Shih et al., Effects of adlay on axoxymethane-induced colon carcinogenesis in rats, Food and Chemical Toxicology, 2004, pp. 1339-1347, vol. 42.

(Continued)

*Primary Examiner* — Susan Hoffman
(74) *Attorney, Agent, or Firm* — WPAT, P.C.; Anthony King; Kay Yang (57) ABSTRACT

The present invention provides a method for treating gastric ulcer and/or stomach cancer in a subject, which comprises administering to said subject an effective amount of an alcohol extract of dehulled adlay seeds. Preferably, an ethyl acetate sub-fraction of the alcohol extract of dehulled adlay seeds has a better effect in treating gastric ulcer and/or stomach cancer.

19 Claims, 6 Drawing Sheets

(56) References Cited

OTHER PUBLICATIONS

Sing-Chung Li et al., Effects of adlay bran and its ethanolic extract and residue on preneoplastic lesions of the colon in rats, J Sci Food Agric, 2011, pp. 547-552, vol. 91.

Cheng-Pei Chung et al., Ethyl Acetate Fraction of Adlay Bran Ethanolic Extract Inhibits Oncogene Expression and Suppresses DMH-Induced Preneoplastic Lesions of the Colon in F344 Rats through an Anti-inflammatory Pathway, Journal of Agricultural and Food Chemistry, 2010, pp. 7616-7623, vol. 58, No. 13.

Hsieh-Hsun Ho et al., Anti-metastasis effects of gallic acid on gastric cancer cells involves inhibition of NF-kB activity and downregulation of PI3K/AKT/small GTPase signals, Food and Chemical Toxicology, 2010, pp. 2508-2516, vol. 48.

Philip G. Reeves, Components of the AIN-93 Diets as Improvements in the AIN-76A diet, The Journal of Nutrition, 1997, p. 838S-841S, vol. 127.

Minako Yoshizawa et al., Protective Effects of Barley and Its Hydrolysates on Gastric Stress Ulcer in Rats, The Pharmaceutical Society of Japan, 2004, pp. 571-575, vol. 124, No. 8.

Hiroshi Ohkawa et al., Assay for Lipid Peroxides in Animal Tissues by Thiobarbituric Acid Reaction, Analytical Biochemistry, 1979, pp. 351-358, vol. 95.

Jozef Sedlak et al., Estimation of Total, Protein-Bound, and Nonprotein Sulfhydryl Groups in Tissue with Ellman's Reagent, Analytical Biochemistry, 1968, pp. 192-205, vol. 25.

\* cited by examiner

ALCOHOL EXTRACT OF DEHULLED ADLAY SEEDS FOR TREATING GASTRIC ULCER AND/OR STOMACH CANCER

BACKGROUND OF THE INVENTION

1. Field of the Invention

The invention relates to uses of an extract of dehulled adlay seeds; more particularly, to the treatment of gastric ulcer and/or stomach cancer.

2. Description of the Related Art

Gastric hyperacidity and gastroduodenal ulcers are a very common global problem today and occur mainly in the stomach and proximal duodenum (Nneli, R. O.; Nwafia, W. C.; Oji, J. O. Niger. *J. Physiol. Sci.* 2007, 22, 1-13). The leading cause of gastric ulcers is an infection by *Helicobacter pylori* (Nneli et al., 2007), while dietary habits, smoking, drinking, and consumption of non-steroidal anti-inflammatory drugs (NSAIDs) were also reported to elevate the risk of gastric ulcers (de Barros, M. P.; Lemos, M.; Maistro, E. L.; Leite, M. F.; Sousa, J. P. B.; Bastos, J. K.; de Andrade, S. F. J. *Ethnopharmacol.* 2008, 120, 372-377). The pathophysiology of these disorders focuses on the aggressive stress and defense mechanism of the stomach, such as hydrochloric acid (HCl) production, mucus secretion, nonprotein sulfhydryl (NPSH) groups from the liver, and blood flow (Nneli et al., 2007). Recent research showed that the ingestion of NSAIDs promotes the production of reactive oxygen species (ROS) and was attributed to increasing oxidative stress in the human body (Das, D.; Bandyopadhyay, D.; Bhattacharjee, M.; Banerjee, R. K. *Free Radical Biol. Med.* 1997, 23, 8-18). ROS play critical roles in the development of acute gastric lesions induced by stress, ethanol, and NSAIDs (Das et al., 1997). In addition, lipid peroxidation of cell membranes induced by ROS causes DNA damage because of the free radicals, and cancer-causing mutations may occur (Halici, M.; Odabasoglu, F.; Sulayman, H.; Cakir, A.; Asian, A.; Bayir, Y. *Phytomedicine* 2005, 12, 656-662.)

Adlay (*Coix lachryma-jobi* L. var. *ma-yuen* Stapf) seeds, also called Job's tears, are a component of traditional Chinese medicine (TCM) and have long been used as an anti-inflammatory agent to treat warts, chapped skin, rheumatism, and neuralgia (Li, S. C. *Pen-t'sao kangmu* (*Systematic Pharmacopoeia*); China, 1596) A recent study showed that dehulled adlay (DA) modulated the microbiota in the intestinal tract of rats (Chiang, W.; Cheng, C.; Chiang, M.; Chung, K. T. *J. Agric. Food Chem.* 2000, 48, 829-832.) Also, the anti-inflammatory and antioxidative effects of adlay were elucidated in vitro (Lee, M. Y.; Tsai, S. H.; Kuo, Y. H.; Chiang, W. *Food Sci. Biotechnol.* 2008, 17, 1265-1271; Kuo, C. C.; Shih, M. C.; Kuo, Y. H.; Chiang, W. *J. Agric. Food Chem.* 2001, 49, 1564-1570) Contents of various potent compounds in adlay seeds from different origins were quantified (Wu, T. T.; Charles, A. L.; Huang, T. C. *Food Chem.* 2007, 104, 1509-1515). Several phenolic antioxidants were isolated from adlay seeds, and bioactive components in adlay seeds were found to be stable during processing (Hsu, H. Y.; Lin, B. F.; Lin, J. Y.; Kuo, C. C.; Chiang, W. *J. Agric. Food Chem.* 2003, 51, 3763-3769) Lignans and phenolic compounds were isolated from adlay hull (AH) in an assay-guided isolation (Kuo, C. C.; Shih, M. C.; Kuo, Y. H.; Chiang, W. *J. Agric. Food Chem.* 2001, 49, 1564-1570). Flavanone and several phenolic acids were isolated from anti-inflammatory fractions of adlay seeds (Huang, D. W.; Kuo, Y. H.; Lin, F. Y.; Lin, Y. L.; Chiang, W. *J. Agric. Food Chem.* 2009, 57, 2259-2266; Huang, D. W; Chung, C. P.; Kuo, Y. H.; Lin, Y. L.; Chiang, W. *J. Agric. Food Chem.* 2009, 57, 10651-10657; Chen, H. J.; Chung, C. P.; Chiang, W.; Lin, Y. L. *Food Chem.* 2011, 126, 1741-1748. Phenolic alcohol in the adlay testa (AT) was reported to possess antiallergic activity (Chen, H. J.; Shih, C. K.; Hsu, H. Y.; Chiang, W. *J. Agric. Food Chem.* 2010, 58, 2596-2601). In addition, DA and adlay bran (AB) were shown to retard carcinogenesis through an anti-inflammatory pathway (Shih, C. K.; Chiang, W.; Kuo, M. L. *Food Chem. Toxicol.* 2004, 42, 1339-1347; Li, S. C.; Chen, C. M.; Lin, S. H.; Chiang, W.; Shih, C. K. *J. Sci. Food Agric.* 2011, 91, 547-552), and ferulic acid was regarded as the active component in a further investigation (Chung, C. P.; Hsu, H. Y.; Huang, D. W.; Hsu, H. H.; Lin, J. T.; Shih, C. K.; Chiang, W. *J. Agric. Food Chem.* 2010, 58, 7616-7623).

Although there are many uses of adlay seeds reported, various applications of extract of adlay seeds remain to be developed.

SUMMARY OF THE INVENTION

In the present invention, the antiproliferative activities against the gastric cancer cell line of extracts from different parts of dehulled adlay are elucidated. The antiulcer effect of dehulled adlay is also provided. This is the first investigation of the gastroprotective activities of adlay seeds.

The invention provides a method for treating gastric ulcer and/or stomach cancer in a subject, which comprises administering to said subject an effective amount of an alcohol extract of dehulled adlay seeds.

DETAILED DESCRIPTION OF THE INVENTION

The invention relates to a method for treating gastric ulcer and/or stomach cancer in a subject, which comprises administering to said subject an effective amount of an alcohol extract of dehulled adlay seeds and optionally a pharmaceutically acceptable carrier or excipient.

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the compounds of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±10%.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder or condition to which such term applies, or one or more symptoms of such disorder or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

Preferably, the alcohol extract of dehulled adlay seeds is comprised in a composition. The composition of the invention is preferably a food composition or a pharmaceutical composition.

The alcohol extract of dehulled adlay seeds can be added to a conventional food composition (i.e. the edible food or drink or precursors thereof) in the manufacturing process of the food composition. Almost all food compositions can be supplemented with the alcohol extract of dehulled adlay seeds of the invention. The food compositions that can be supplemented with the alcohol extract of dehulled adlay seeds of the invention include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The pharmaceutical composition of the invention is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art; see paragraph [0022] for example.

Figure 1:
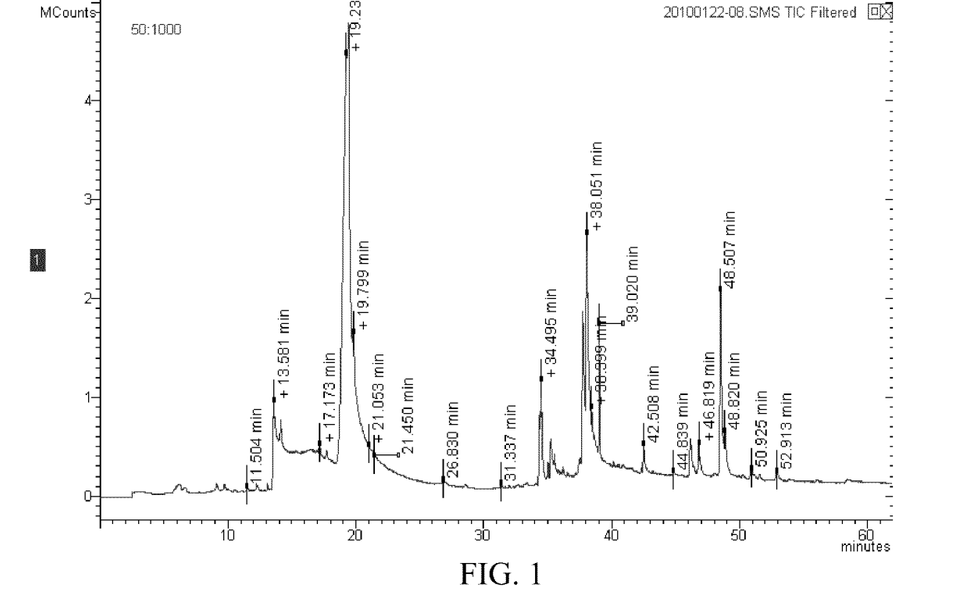
FIG. 1 illustrates the GC-MS spectrogram of the alcohol extract of dehulled adlay seeds according to the invention.

In one preferred embodiment of the invention, the alcohol extract of dehulled adlay seeds is subjected to a Gas Chromatography-Mass Spectrophotometry (GC-MS) assay. The gas chromatography is conducted with Varian® 450-GC; and the mass spectrophotometry is conducted with Varian® 240-MS; the column is Varian® VF-5 ms 30 m×0.25 mm (I.D. 0.25 μm). The temperature program is 150° C. for 5 min; heating to 200° C. at a rate of 10° C./min for 20 min; and heating to 280° C. at a rate of 10° C./min for 25 min. As shown in FIG. 1, the spectrogram obtained comprises peaks at retention time of about 13.581 min, about 19.237 min, 19.334 min, about 19.435 min, about 19.799 min, about 37.75 min, about 38.051 min, about 48.504 min and about 48.819 min (Table 1).

TABLE 1

| Retention time (min) | Area (%) |
|---|---|
| 13.581 | 2.65 |
| 19.237 | 35.17 |
| 19.334 | 6.68 |
| 19.435 | 20.60 |
| 19.799 | 4.11 |
| 37.75 | 7.70 |
| 38.051 | 11.94 |
| 48.504 | 8.56 |
| 48.819 | 2.60 |

Figure 2:
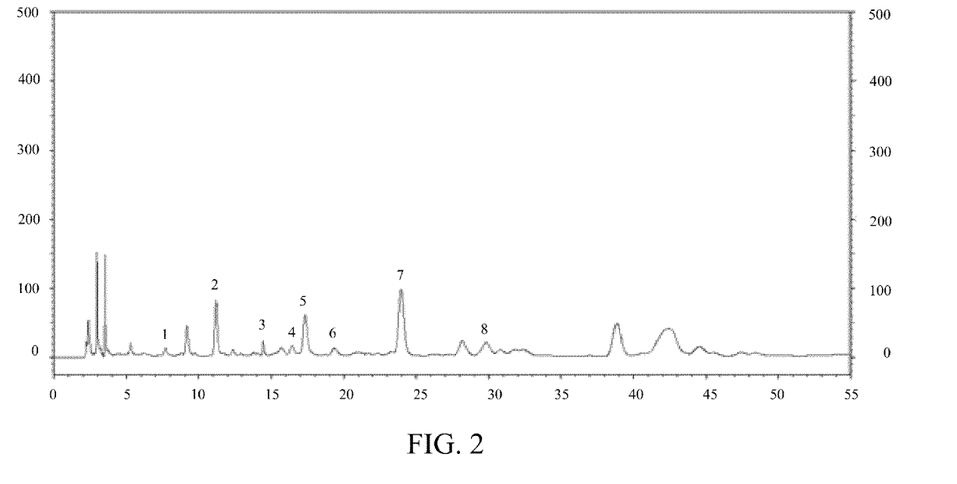
FIG. 2 illustrates the HPLC spectrogram of the alcohol extract of dehulled adlay seeds according to the invention.

In one preferred embodiment of the invention, the alcohol extract of dehulled adlay seeds is subjected to a high performance liquid chromatography assay. The column is Reverse phase C18 column (250×4.6 mm i.d.; YMC Co., INC). The column temperature is 40° C. The chromatograms are extracted at 280 nm and 320 nm. The mobile phase uses Solution A: 5% acetic acid in water; Solution B: 0.5% acetic acid in water/100% acetonitrile (1:1, v/v). The gradient elution program is shown in Table 2. As shown in FIG. 2, the spectrogram obtained comprises peaks at retention time of about 7.5 min, about 12.1 min, 14.4 min, about 16.1 min, about 16.8 min, about 18.9 min, about 23.3 min, and about 29.1 min.

TABLE 2

| Time (min) | Flow rate (mL/min) | Mobile phase A (%) | Mobile phase B (%) |
|---|---|---|---|
| 0 | 1.0 | 90 | 10 |
| 10 | 1.0 | 85 | 15 |
| 20 | 1.0 | 84 | 16 |
| 35 | 1.0 | 83 | 17 |
| 50 | 1.0 | 79 | 21 |
| 55 | 1.0 | 79 | 21 |

The dehulled adlay seeds comprises bran and endosperm, therefore, the alcohol extract of dehulled adlay seeds according to the invention preferably comprises an alcohol extract of adlay bran and an alcohol extract of adlay endosperm. The manner for obtaining the bran and endosperm from the dehulled adlay seeds is well-known to artisans skilled in this field.

In one preferred embodiment of the invention, the alcohol extract of dehulled adlay seeds is an ethanol extract of dehulled adlay seeds.

In one preferred embodiment of the invention, the method comprises administering to said subject an effective amount of an ethyl acetate sub-fraction of the alcohol extract of dehulled adlay seeds.

In one preferred embodiment of the invention, the method comprises administering to said subject an effective amount of an ethyl acetate sub-fraction of the alcohol extract of adlay bran.

In one preferred embodiment of the invention, the method comprises administering to said subject an effective amount of an n-butanol sub-fraction of the alcohol extract of adlay bran.

In one preferred embodiment of the invention, the method comprises administering to said subject an effective amount of an ethyl acetate sub-fraction of the alcohol extract of adlay endosperm.

In one preferred embodiment of the invention, the alcohol extract of dehulled adlay seeds is prepared according to a process comprising:
(a) providing dehulled adlay seeds;
(b) cutting the dehulled adlay seeds into small pieces; and
(c) extracting the small pieces in step (b) with the alcohol to obtain an extract.

The term "dehulled adlay seeds" as used herein refers to seeds of adlay without hulls, testas, coverings, shells, or pods. The manner of removing the hulls, coverings, shells or pods from the adlay seeds is well-known to artisans skilled in this field. If needed, the bran and/or endosperm is further isolated from the dehulled adlay seeds.

The adlay seeds referred to in this invention are not particularly limited. Preferably, the adlay belongs to Gramineae family, Panicoideae sub-family, and *Coix* species, or Poales order, Poaceae family, and *Coix* species. More preferably, the adlay is *Coix lachryma-jobi, Coix lachryma-jobi* L., *Coix lachryma-jobi* L. var. *ma-yuen* Stapf, *Coix agrestis* Lour., *Coix arundinacea* Lam., *Coix exaltata* Jacq., *Coix lacryma* L.

According to the process of the invention, prior to step (b), the dehulled adlay seeds are preferably dried.

In one preferred embodiment of the invention, step (b) further comprises blending the small pieces into powder. The manner of cutting and/or blending is well-known to artisans skilled in this field.

The term "an alcohol extract of dehulled adlay seeds" as used herein refers to an extract of dehulled adlay seeds obtained by extracting the seeds with an alcohol solution. The manner of extracting the seeds with a solution is well-known to artisans skilled in this field. In one preferred embodiment of the invention, the dehulled adlay seeds are soaked in an alcohol solution for extraction.

The ratio (w/v) of the dehulled adlay seeds and the alcohol solution is not specifically restricted, and can be about 1:1 to about 1:10; preferably about 1:3 to about 1:8; and most preferably about 1:5.

In one preferred embodiment of the invention, the alcohol is selected from the group consisting of methanol, ethanol, n-propanol, isopropanol, n-butanol, iso-butanol, sec-butanol, tert-butanol, and ethanol acetate. More preferably, the alcohol is methanol or ethanol; most preferably, the alcohol is ethanol. The alcohol solution preferably about 90% to about 99.9% ethanol.

Preferably, the process further comprises (d) obtaining a liquid fraction from the extract, and a solid fraction is removed. The manner of removing the solid fraction to obtain the liquid fraction is well-known to artisans skilled in this field.

In one preferred embodiment of the invention, an ethyl acetate or n-butanol sub-fraction of the alcohol extract of dehulled adlay seeds is prepared by further extracting the alcohol extract of dehulled adlay seeds. In one preferred embodiment of the invention, the process for preparing the alcohol extract of dehulled adlay seeds further comprises (e) extracting the liquid fraction with ethyl acetate or n-butanol.

The alcohol extract of dehulled adlay seeds and preferably the ethyl acetate sub-fraction of the alcohol extract of dehulled adlay seeds are effective on treating gastric ulcer and/or stomach cancer in a subject. More preferably, the gastric ulcer is non-steroidal anti-inflammatory drugs induced gastric ulcer. In another aspect, the alcohol extract of dehulled adlay seeds and preferably the ethyl acetate sub-fraction of the alcohol extract of dehulled adlay seeds are effective on inhibiting the growth of stomach cancer.

The following examples are given for the purpose of illustration only and are not intended to limit the scope of the present invention.

Example

Materials and Methods

Drugs and Reagents.

Adlay seeds were purchased from local farmers who planted Taichung Shuenyu no. 4 (TCS4) of *C. lachrymajobi* L. var. *ma-yuen* Stapf in Taichung, Taiwan, in 2009. The AGS cell line was obtained from the Bioresource Collection and Research Center (Hsinchu, Taiwan). 3-(4,5-Dimethyl-2-thiazolyl)-2,5-diphenyl-2H-tetrazolium bromide (MTT), 2-thiobarbituric acid (TBA), butylated hydroxytolune (BHT), 1,1,3,3-tetraethoxypropane (TEP), indomethacin, trichloroacetic acid (TCA), 5,50-dithiobis-2-nitrobenzoic acid (DTNB), alcian blue, L-cysteine hydrochloride, sodium chloride (NaCl), sodium phosphotungstate tribasic hydrate, potassium carbonate ($K_2CO_3$), trizma base, magnesium chloride ($MgCl_2$), carboxymethyl cellulose (CMC), and the standards used in the assays were obtained from Sigma Chemicals (St. Louis, Mo.). Antibiotics, fetal bovine serum (FBS), and Dulbecco's modified Eagle's medium (DMEM) were purchased from GIBCO (Grand Island, N.Y.). Analytical-grade solvents used during the purification procedures, including methanol (MeOH), ethanol (EtOH), n-hexane (Hex), ethyl acetate (EA), 1-butanol (BuOH), acetone (ACE), dichloromethane ($CH_2Cl_2$), and dimethyl sulfoxide (DMSO) used for stock solution of in vitro studies, were purchased from Merck®.

Extraction and Fractionation.

AH and AT were removed from adlay seeds with a grinder. The dehulled adlay (DA), adlay bran (AB), and adlay endosperm (AE) were further ground into a powder and soaked in 5-fold 95% EtOH (w/v) at room temperature for 48 h. The extracts were combined and concentrated under reduced pressure at 50° C. to give the DA ethanolic extract (DAE, 2.35% of DA), AB ethanolic extract (ABE, 8.09% of AB), and AE ethanolic extract (AEE, 2.65% of AE). The ABE was suspended in water, which was followed by sequential partitioning with Hex, EA, and BuOH to give the Hex-soluble fraction (ABE Hex, 60.7% of ABE), EA-soluble fraction (ABE EA, 7.2% of ABE), BuOH-soluble fraction (ABE BuOH, 4.4% of ABE), and water-soluble fraction (ABE $H_2O$, 27.2% of ABE) according to the reported literature (Chung, C. P.; Hsu, H. Y.; Huang, D. W.; Hsu, H. H.; Lin, J. T.; Shih, C. K.; Chiang, W. *J. Agric. Food Chem.* 2010, 58, 7616-7623). In addition, the AB methanolic extract (ABM, 16.5% of AB), ABM EA (14.3% of ABM), and ABM BuOH (13.7% of ABM) were obtained as previously described (Lee, M. Y.; Tsai, S. H.; Kuo, Y. H.; Chiang, W. *Food Sci. Biotechnol.* 2008, 17, 1265-1271).

Cell Culture and Antiproliferation Assay.

The AGS cell line was cultured in DMEM containing 10% heat-inactivated FBS, 100 units/mL penicillin, and 100 µg/mL streptomycin with a 5% $CO_2$ atmosphere at 37° C. (Ho, H. H.; Chang, C. S.; Ho, W. C.; Liao, S. Y.; Wu, C. H.; Wang, C. *J. Food Chem. Toxicol.* 2010, 48, 2508-2516). To determine the antiproliferative effect, AGS cells were assessed using a MTT assay as previously described (Ho, H. H. et al., 2010). Test samples were dissolved in DMSO, and the final concentration of DMSO was ≤0.1%. AGS cells were cultured in 96-well plates at a density of $2\times10^3$ cells/well and allowed to grow for 24 h. After this, the medium was replaced with FBS-free DMEM, then various test samples were added, and cells were incubated for an additional 48 h. Next, a MTT solution in FBS-free DMEM, which had been filtered through a 0.45 mm membrane, was added to each well (to a final concentration of 1 mg/mL). The plates were incubated under a 5% $CO_2$ atmosphere at 37° C. for 4 h. The medium with unreacted dye was removed. DMSO (100 µL) was added to each well to dissolve the MTT formazan crystals, and the absorbance at 570 nm was measured. The viability of cells was calculated using the following equation: relative cell viability (%)=(average of absorbance of treated wells)×100/(average of absorbance of untreated wells). DMSO at 0.1% was used as the blank vehicle.

Animal Diets and NSAID-Induced Gastric Ulcer Model.

The study protocol was approved by the Institutional Animal Care and Use Committee (IACUC) of National Taiwan University. A total of 32 male Wistar rats (5 weeks of age) were purchased from the Animal Center of the College of Medicine at National Taiwan University (Taipei, Taiwan). Animals were individually housed in plastic cages in a pathogen-free room at 23±2° C. and 50±10% relative humidity with a 12 h light/dark cycle and were fed a standard AIN-93 M diet (Reeves, P. G. *J. Nutr.* 1997, 127, 838S-841S) and water ad libitum before the experimental period began. Ingredients in the experimental diets were substituted with DA as previously described (Hsu, H. Y. et al., 2003; Shih, C. K. et al., 2004). Rats were weighed, and food consumption was recorded twice a week. The rats were randomly divided into four groups: a blank group (BL) and a negative control group (NC) comprised of 8 rats each maintained on a standard AIN-93 M diet, a low-dose DA group (LDA) consisting of 8 rats on a 10% DA-substituted AIN-93 M diet, and a high-dose DA group (HDA) consisting of 8 rats on a 30% DA-substituted AIN-93 M diet (Table 3A). Animals were maintained on the test diets for 4 weeks and then starved for 36 h. To induce gastric ulcers, a previously described method was used with a few modifications (de Barros, M. P. et al., 2008). Indomethacin at 30 mg/kg of body weight was dissolved in a 0.5% CMC aqueous solution, which was used to induce gastric ulcers, while the BL group was given 0.5% of the CMC vehicle. After treatment with indomethacin or vehicle for 7 h, rats were sacrificed. The stomach, liver, and serum were obtained and stored at −20° C. for further analysis.

TABLE 3

(A) DA-Containing Experimental Diets and (B) Effects on Body Weight, Feed Efficiency, and Liver Weight in Wistar Rats.

(A)

| diet constituents | BL (g/kg of experimental diet) | NC (g/kg of experimental diet) | LDA (g/kg of experimental diet) | HDA (g/kg of experimental diet) |
|---|---|---|---|---|
| cornstarch | 397.49 | 397.49 | 329.20 | 192.59 |
| casein | 200.00 | 200.00 | 178.70 | 136.10 |
| dextrinized cornstarch | 132.00 | 132.00 | 132.00 | 132.00 |

TABLE 3-continued (A) DA-Containing Experimental Diets and (B) Effects
on Body Weight, Feed Efficiency, and Liver Weight in Wistar Rats.

| | | | | |
|---|---|---|---|---|
| sucrose | 100.00 | 100.00 | 100.00 | 100.00 |
| soybean oil | 70.00 | 70.00 | 61.70 | 45.10 |
| alphacel, non-nutritive bulk | 50.00 | 50.00 | 50.00 | 50.00 |
| AIN-93 M mineral mix | 35.00 | 35.00 | 35.00 | 35.00 |
| L-cystine | 10.00 | 10.00 | 10.00 | 10.00 |
| AIN-93 vitamin mix | 3.00 | 3.00 | 3.00 | 3.00 |
| choline bitartrate | 2.50 | 2.50 | 2.50 | 2.50 |
| tert-butyhydroquinone (TBHQ) | 0.01 | 0.01 | 0.01 | 0.01 |
| DA | | | 100.00 | 300.00 |

(B)

| | Groups[a] | | | | |
|---|---|---|---|---|---|
| parameters[b] body weight (g) | | BL | parameters[b] body weight (g) | BL | parameters[b] body weight (g) |
| initial | 346 ± 18 | | initial | 346 ± 18 | initial |
| final | 466 ± 25 | | final | 466 ± 25 | final |
| feed intake (g/day) | 23.5 ± 0.0 | | feed intake (g/day) | 23.5 ± 0.0 | feed intake (g/day) |
| feed effciency[c] (%) | 19.6 ± 7.1 | | feed effciency[c] (%) | 19.6 ± 7.1 | feed effciency[c] (%) |
| liver weight (g) | 10.8 ± 0.4 | | liver weight (g) | 10.8 ± 0.4 | liver weight (g) |

[a]BL, control group; NC, negative control group; LDA, low-dose DA group; and HDA, high-dose DA group.
[b]All values are presented as the mean + SD (n = 8).
[c]Feed efficiency = (body weight gained/total feed intake) × 100.

Determination of the Gastric Ulcer Index (UI), TBA Reactive Substances (TBARS), NPSH, and Pathological Observations of the Stomachs.

Total blood was collected before the stomach was surgically removed by an abdominal incision. After being rinsed in phosphate-buffered saline (PBS), the stomach was opened and extended, so that it could be photographed. Areas with erosion were analyzed by Image software designed by the National Institute of Health (NIH, Bethesda, Md.) as the UI (mm$^2$) (Yoshizawa, M.; Yokoyama, K; Nakano, Y.; Nakamura, H. Pharm. Soc. Jpn. 2004, 124, 571-575) The mucus was removed by a slide immediately after being photographed. Then, the tissues were fixed in 10% formalin and stored at 4° C. The fixed samples were dehydrated and defatted using various concentrations of EtOH, then embedded in paraffin, and exterminated to 3-4 μm section slices. Paraffin in the slices was eliminated, and the sections were stained with hematoxylin and eosin (H&E). Histopathological changes were observed using an optical microscope. Mucus or liver tissue (0.2 g) was mixed with 2 mL of 0.15 M NaCl with 0.002% BHT solution or 2 mL of a 0.02 Methylenediaminetetra acetic acid (EDTA)-Na$_2$ solution and then homogenized in a blender, and the homogenates were stored at 20° C. for further analysis.

Serum and gastric mucosal TBARS were examined as previously described (Ohkawa, H.; Ohichi, N.; Yagi, K. Anal. Biochem. 1979, 95, 351-358). Briefly, 20 μL of serum was mixed with 4 mL of 1/12 N sulfuric acid aqueous solution and allowed to stand at room temperature for 5 min after adding 0.5 mL of a 10% sodium phosphotungstate aqueous solution. The supernatants were removed after centrifugation at 1570 g for 15 min, and the pellets were mixed with 4 mL of double-distilled (dd) water and 1 mL of a 0.67% TBA solution. The samples were placed in a water bath at 95° C. for 60 min. After cooling, 5 mL of BuOH was added to the test samples and centrifuged at 1570 g for 15 min. The supernatants were measured by a fluorescence spectrometer (F-4500, Hitachi, Japan) (with excitation at 515 nm and emission at 553 nm), and the results were recorded as absorbance units (AU). Likewise, 0.2 mL of the gastric mucus homogenate was mixed with 0.2 mL of 1.15% KCl/3 mM EDTA Na$_2$, 3 mL of 1% H$_3$PO$_4$, 0.3 mL of 0.3% BHT/EtOH, and 1 mL of a 0.6% TBA solution. Test samples were placed in a water bath at 100° C. for 60 min after being vortex-mixed. BuOH (2 mL) was added to cooled samples, and the absorbance of the BuOH fraction was measured at 532 nm. The calibration curve was established using various concentrations of TEP solutions. Results were recorded as nanomoles per gram of tissue.

A previously described method (Sedlek, J.; Lindsay, R. H. Anal. Biochem. 1968, 25, 192-205) was used to examine the NPSH in the gastric mucus and liver. Briefly, 1 mL of gastric mucus or liver homogenate was mixed with 0.8 mL of dd water and 0.5 mL of a 50% TCA solution. After vortex-mixing for 2 min, the solutions were centrifuged at 1570 g for 20 min. Supernatants (0.5 mL) were mixed with 1.0 mL of 0.4M Tris-buffer (pH 8.9) and colored by 25 μL of a 0.01 M DTNB solution. The absorbance at 412 nm was recorded, and the results are presented as micromoles per gram of tissue.

Statistical Analysis. All values are presented as the mean±standard deviation (SD). Results of the various groups were analyzed by an analysis of variance (ANOVA) and Duncan's multiple-range test. p values of <0.05 were considered statistically significant.

Results and Discussion

Antiproliferative Activities of DAE, ABE, and Partitioned Fractions from ABE and AEE.

Figure 3:
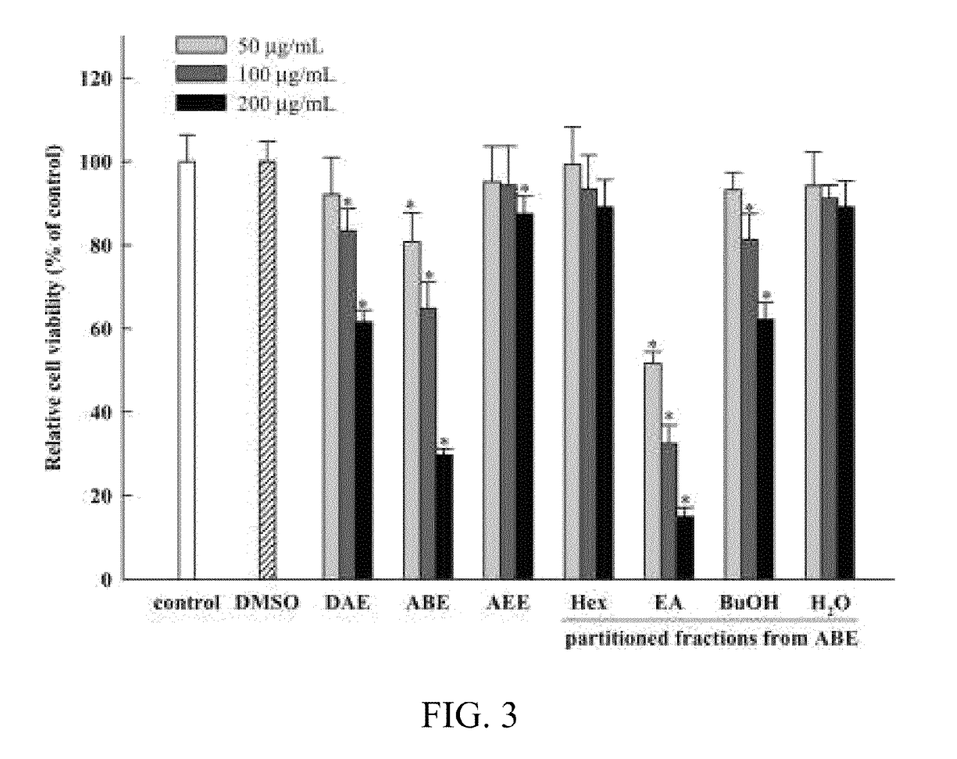
FIG. 3 shows the effects of DAE, ABE, AEE, and partitioned fractions from ABE on cell proliferation in the AGS cell line. Cells were cultured with or without test samples for 48 h and examined using a MTT assay. The results are expressed as a percentage of living cells cultured in the presence of the test samples relative to a parallel culture that receives no treatment. Each bar represents the mean±SD (n=3), and bars with different letters differ significantly. (*) $p<0.05$ compared to the control group.

To evaluate the antiproliferative effects on AGS cells of DA, DAE, ABE, and AEE were prepared. DAE inhibited 38.5% of AGS cell viability at 200 μg/mL, and ABE suppressed 71.0% of cell growth under treatment with 200 μg/mL, while AEE showed lower activity (FIG. 3). The results demonstrated that AB contributes to a major part of the antiproliferative effect of DA. The inhibitory activities of the partitioned fractions were also examined against AGS cells. The suppressive 50% inhibitory concentration (IC$_{50}$) of ABE EA was <100 μg/mL, while ABE BuOH inhibited 37.9% of cell growth at 200 μg/mL (FIG. 3). The results showed that ABE EA and ABE BuOH possessed higher activities than the other fractions.

Effects of DA on Animals with Indomethacin-Induced Gastric Ulcers.

Figure 4:
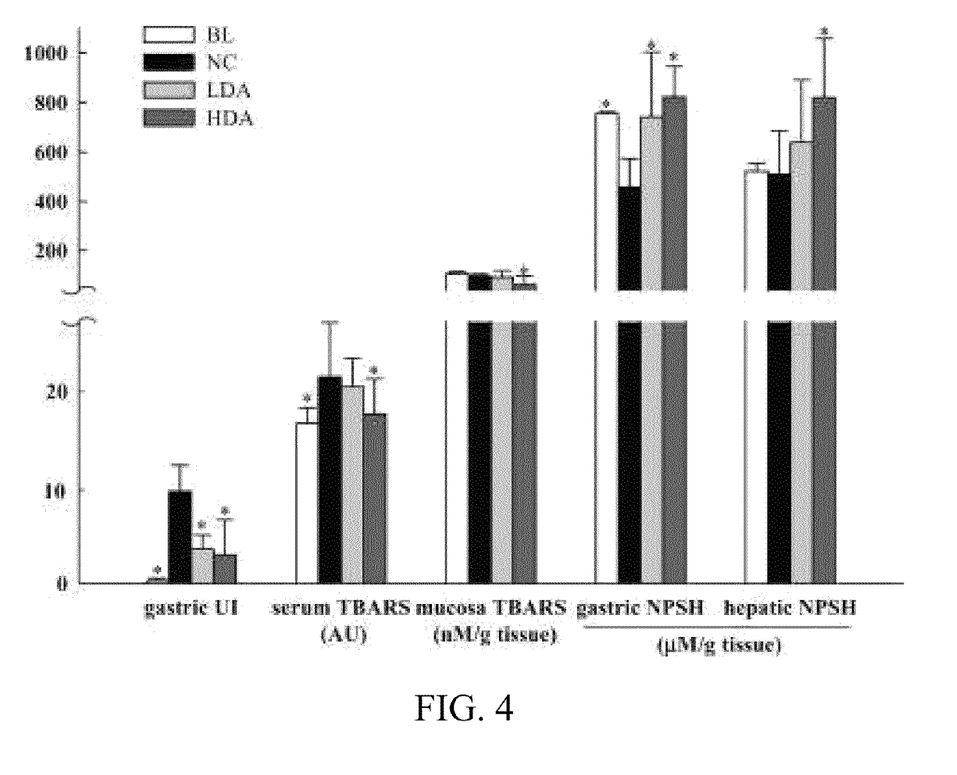
FIG. 4 shows the influence on the UI, serum and mucosal TBARS, and mucosal and hepatic NPSH groups of indomethacin-treated Wistar rats administrated DA. Each bar represents the mean±SD (n=8), and bars with different letters differ significantly. The break omits 28_40. (*) $p<0.05$ compared to the NC group. BL, blank group; NC, negative control group; LDA, low-dose DA group; and HDA, high-dose DA group.
Figure 5:
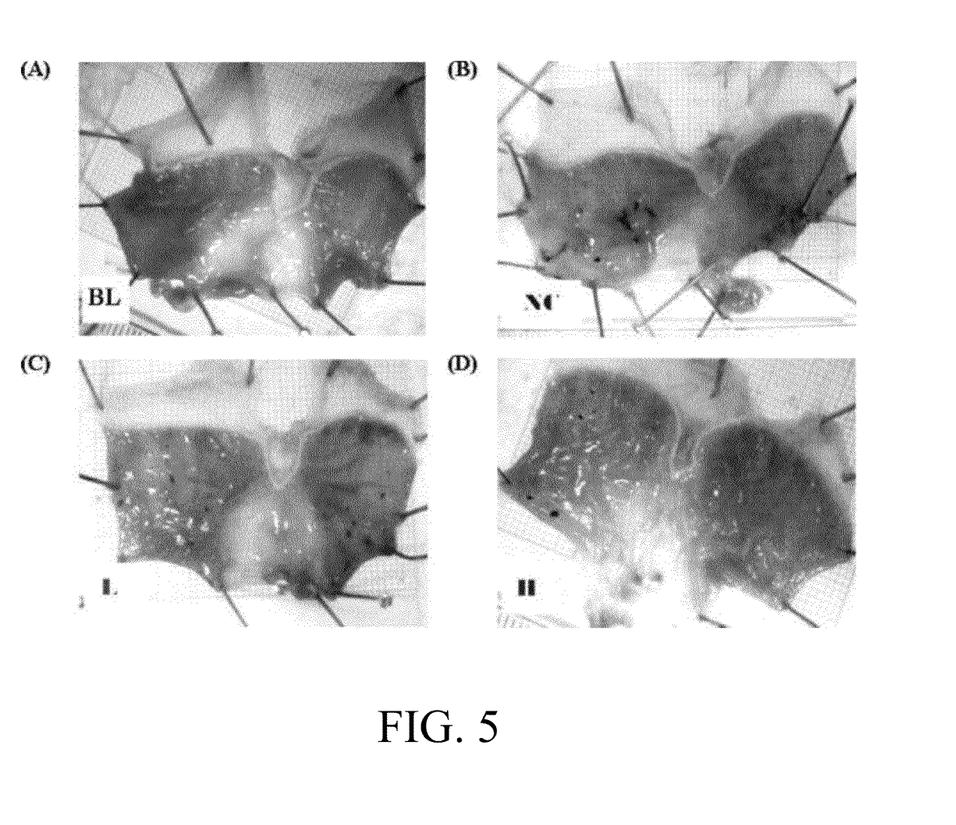
FIG. 5 shows the pathological changes in the stomachs of male Wistar rats with indomethacin-induced gastric ulcers: (A) blank group, (B) negative control group, (C) LDA group, and (D) HDA group.
Figure 6:
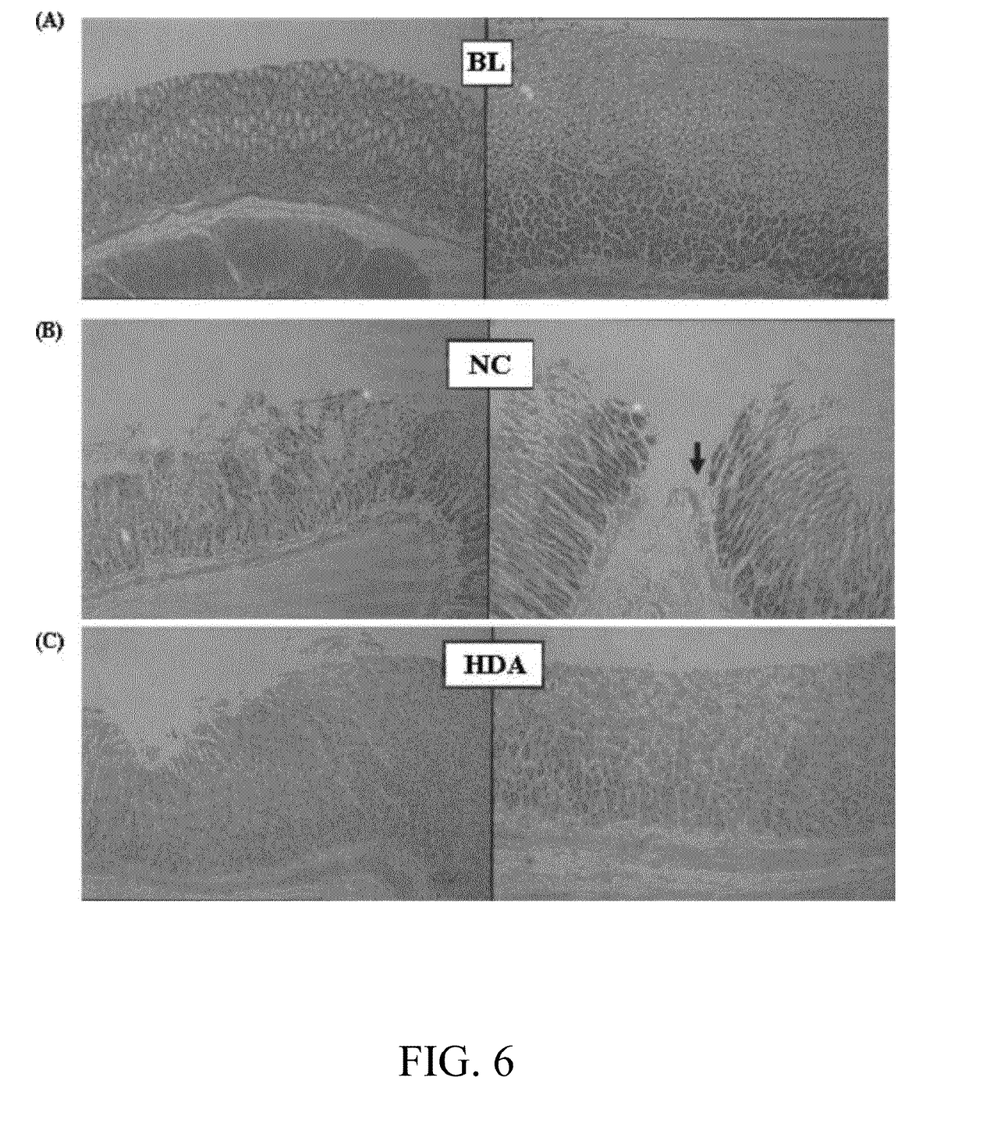
FIG. 6 shows the histopathological observations of H&E-stained sections in the stomach of Wistar rats: (A) blank group, (B) negative control group, and (C) HDA group (left, 60×; right, 100×). The black arrow indicates erosion because of ulceration.

Rats administrated DA were treated with indomethacin to induce gastric ulcer as previously described (de Barros, M. P. et al., 2008). The AIN-93M standard (Reeves, P. G. 1997) was modified, while 10 and 30% DA contents were integrated into ANI-93 M ingredients as previously described, including crude fat, crude protein, and a nitrogen-free extract (NFE), to ensure that the calories were the same for all experimental groups (Hsu, H. Y. et al., 2003; Shih, C. K. et al., 2004) (Table 3A). After 4 weeks of the experimental period, the final body weights, average food intake levels, feed efficiencies, and liver weights did not differ significantly among all groups (Table 3B). The results demonstrated that DA did not retard normal growth of the animals. The UI decreased with administration of DA, which was significantly suppressed compared to the NC group (FIG. 4). Numbers of bleeding clots on the surface of the stomach of the LDA and HAD groups were fewer than those of the NC group, while they were not seen in the BL group (FIG. 5). Stomachs from the BL, NC, and HAD groups were investigated by histopathological observations. The results showed that the erosion was severe in the NC group, while it was inhibited when DA was given (FIG. 6).

To investigate the mechanism of the antiulcer effects, several indicators were analyzed in the present study. Serum TBARS was elevated in the NC group compared to the BL group and was lower in the HAD group compared to the NC group, while that in the LDA group was not significant (FIG. 4). Mucosal TBARS did not show significant differences among the BL, NC, and LDA groups but was lower in the HDA group (FIG. 4). The gastric NPSH was lower in the NC group compared to the BL group, while DA raised the NPSH to a normal status compared to the NC group (FIG. 4). The hepatic NPSH did not change when treated with indomethacin but was elevated in the HDA group compared to the NC and BL groups (FIG. 4). Our results showed that DA suppressed levels of serum and mucosal TBARS, while it increased gastric and hepatic NPSH, which means that the antioxidative capacity of DA is mainly responsible for its antiulcer activity.

In conclusion, we demonstrated the gastroprotective effects of DA. AB showed better antiproliferative activity against AGS cells than AE. In addition, DA inhibited indomethacin-induced gastric ulcers through antioxidative pathways.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A method for treating gastric ulcer and/or stomach cancer in a subject, which consists of administering to said subject an effective amount of an alcohol extract of dehulled adlay seeds and a pharmaceutically acceptable carrier or excipient.

2. The method according to claim 1, wherein the alcohol extract of dehulled adlay seeds comprises an ethanol extract of adlay bran and an alcohol extract of adlay endosperm.

3. The method according to claim 1, wherein the alcohol extract of dehulled adlay seeds is an alcohol extract of adlay bran and an alcohol extract of adlay endosperm.

4. The method according to claim 1, where an effective amount of an ethyl acetate sub-fraction of the alcohol extract of dehulled adlay seeds is administered to said subject.

5. The method according to claim 1, where an effective amount of an ethyl acetate sub-fraction of the alcohol extract of adlay bran is administered to said subject.

6. The method according to claim 1, where an effective amount of an n-butanol extract sub-fraction of the alcohol extract of adlay bran is administered to said subject.

7. The method according to claim 1, where an effective amount of an ethyl acetate sub-fraction of the alcohol extract of adlay endosperm is administered to said subject.

8. The method according to claim 1, wherein the alcohol extract of dehulled adlay seeds is prepared according to a process comprising:
(a) providing dehulled adlay seeds;
(b) cutting the dehulled adlay seeds into small pieces; and
(c) extracting the small pieces in step (b) with the alcohol to obtain an extract.

9. The method according to claim 1, wherein the adlay is *Coix lachryma-jobi* L. var. *ma-yuen* Stapf.

10. The method according to claim 1, wherein the alcohol is selected from the group consisting of methanol, ethanol, n-propanol, isopropanol, n-butanol, iso-butanol, sec-butanol, tert-butanol, and ethanol acetate.

11. The method according to claim 1, wherein the alcohol is ethanol.

12. The method according to claim 8, wherein step (b) further comprises blending the small pieces into powder.

13. The method according to claim 8, wherein the process further comprises (d) obtaining a liquid fraction from the extract.

14. The method according to claim 13, wherein the process further comprises (e) extracting the liquid fraction with ethyl acetate.

15. The method according to claim 13, wherein the process further comprises (e) extracting the liquid fraction with n-butanol.

16. The method according to claim 1, wherein the gastric ulcer is non-steroidal anti-inflammatory drugs-induced gastric ulcer.

17. The method according to claim 1, which is for inhibiting the growth of stomach cancer.

18. A method for treating gastric ulcer and/or stomach cancer in a subject, which comprises:
administering to said subject an effective amount of an alcohol extract of dehulled adlay seeds, and
administering to said subject an effective amount of an ethyl acetate sub-fraction of the alcohol extract of dehulled adlay seeds.

19. A method for treating gastric ulcer and/or stomach cancer in a subject, which comprises:
administering to said subject an effective amount of an alcohol extract of dehulled adlay seeds, and
administering to said subject an effective amount of an n-butanol sub-fraction of the alcohol extract of adlay bran.

* * * * *